US011559288B2

(12) United States Patent
Perdue et al.

(10) Patent No.: US 11,559,288 B2
(45) Date of Patent: Jan. 24, 2023

(54) PORTABLE FLUID SAMPLING DEVICE, SYSTEM FOR USING SAME, AND METHOD OF MAKING AND USING SAME

(71) Applicant: CSP TECHNOLOGIES, INC., Auburn, AL (US)

(72) Inventors: Ethan Ross Perdue, Auburn, AL (US); G. F. Alexia Gleason, Auburn, AL (US); Gary Peters, Auburn, AL (US)

(73) Assignee: CSP Technologies, Inc., Auburn, AL (US)

( * ) Notice: Subject to any disclaimer, the term of this patent is extended or adjusted under 35 U.S.C. 154(b) by 293 days.

(21) Appl. No.: 16/759,088

(22) PCT Filed: Oct. 24, 2018

(86) PCT No.: PCT/US2018/057219
§ 371 (c)(1),
(2) Date: Apr. 24, 2020

(87) PCT Pub. No.: WO2019/084092
PCT Pub. Date: May 2, 2019

(65) Prior Publication Data
US 2021/0177382 A1 Jun. 17, 2021

Related U.S. Application Data

(60) Provisional application No. 62/619,983, filed on Jan. 22, 2018, provisional application No. 62/576,607, filed on Oct. 24, 2017.

(51) Int. Cl.
*A61B 5/097* (2006.01)
*A61B 10/00* (2006.01)
*G01N 1/22* (2006.01)

(52) U.S. Cl.
CPC .......... *A61B 10/0045* (2013.01); *A61B 5/097* (2013.01); *A61B 2010/0087* (2013.01); *G01N 2001/2244* (2013.01)

(58) Field of Classification Search
CPC . A61B 5/082; A61B 5/097; A61B 2010/0087; A61B 5/093; A61B 5/0935;
(Continued)

(56) References Cited

U.S. PATENT DOCUMENTS

| 5,826,575 A | 10/1998 | Lall |
| 2002/0066780 A1* | 6/2002 | Balolia .................. G07C 13/00 235/51 |

(Continued)

FOREIGN PATENT DOCUMENTS

| EP | 1075659 A1 | 2/2001 |
| EP | 2518499 A1 | 10/2012 |
| WO | 2017091134 A1 | 1/2017 |

OTHER PUBLICATIONS

International Search Report of PCT/US2018/057219, dated Mar. 25, 2019.

*Primary Examiner* — Herbert K Roberts
(74) *Attorney, Agent, or Firm* — Mark T. Vogelbacker; Eckert Seamans Cherin & Mellott, LLC (57) ABSTRACT

A system for collecting and retaining a sample from exhaled breath of a subject for analysis can include a two part housing, a two part trap section, and optionally a boat fitment. Disclosed is a portable fluid sampling device comprising: a housing including a first portion removably attachable to a second portion, the first and second portions being configured to combine to form a chamber therein, the chamber being configured to at least temporarily contain or hold a biological sample therein, at least one of the first portion and the second portion including an inlet, the other of the first portion and the second portion including an
(Continued)

outlet, wherein the device further comprises at least one of the following: a) one of the first portion and the second portion including an end having a projection, the other of the first portion and the second portion including an end having a groove, the groove being configured to receive at least a portion of the projection therein; or b) tamper evident means for indicating that the first portion of the housing has previously been separated from the second portion of the housing.

16 Claims, 11 Drawing Sheets (58) Field of Classification Search
CPC ....... A61B 5/095; A61B 5/083; A61B 5/0833; A61B 5/0836; G01N 33/497; G01N 33/4972; G01N 33/98; G01N 2033/4975; G01N 2033/4977; G01N 2001/2244
See application file for complete search history.

(56) References Cited

U.S. PATENT DOCUMENTS

| | | | |
|---|---|---|---|
| 2009/0187113 A1* | 7/2009 | Friedman | A61B 5/097 600/543 |
| 2013/0133663 A1* | 5/2013 | Maksym | A61M 16/0057 128/205.27 |
| 2014/0366609 A1* | 12/2014 | Beck | G01N 33/497 73/23.3 |
| 2015/0033824 A1 | 2/2015 | Hammarlund et al. | |
| 2016/0262657 A1* | 9/2016 | Ahmad | A61B 5/7271 |
| 2017/0021122 A1 | 1/2017 | Wisniewski | |

* cited by examiner

PORTABLE FLUID SAMPLING DEVICE, SYSTEM FOR USING SAME, AND METHOD OF MAKING AND USING SAME

CROSS-REFERENCE TO RELATED APPLICATIONS

The present application is a National Phase of PCT/US2018/057219 filed Oct. 24, 2018 and titled "PORTABLE FLUID SAMPLING DEVICE, SYSTEM FOR USING SAME, AND METHOD OF MAKING AND USING SAME," which claims priority to U.S. Provisional Application No. 62/576,607 filed Oct. 24, 2017 and titled "PORTABLE SAMPLING DEVICE AND SYSTEM FOR USING THE SAME," and U.S. Provisional Application No. 62/619,983 filed Jan. 22, 2018 and titled "PORTABLE SAMPLING DEVICE, SYSTEM FOR USING SAME, AND METHOD OF MAKING AND USING SAME," all of which are hereby incorporated by reference in their entirety.

FIELD

The presently disclosed technology relates generally to the field of portable handheld devices, sampling systems and methods for collecting a sample from exhaled breath of a subject, and/or for detecting the presence (i.e., qualitative) and/or determining the quantitative amount of at least one specific and/or illicit drug, substance or compound in exhaled breath. More particularly, in one embodiment, the presently disclosed technology relates to improved construction of such devices.

DESCRIPTION OF RELATED ART

Exhaled breath is commonly used in alcohol testing, for example, and the prior art makes it possible to perform on-site breath testing with legally defensible results using infrared spectroscopy. In addition, systems and methods are known for detecting the presence or amount of at least one biomarker for medical diagnosis of a subject or the presence of certain drug substances that the subject had taken. For example, U.S. Pat. Pub. No. 2014/0366609 and U.S. Pat. Pub. No. 2015/0033824, which are incorporated by reference herein in their entireties, disclose portable drug sampling devices configured for receiving and containing the exhaled breath of a subject.

Sensabues AB is a Swedish company that produces an exhaled breath-based biomatrix platform, which they refer to as ExaBreath® or EB. EB is configured to facilitate collection of exhaled breath for detection and identification of nonvolatile substances in a subject's blood. EB may be used, for example, to detect the presence of exogenous substances in a subject's blood, such as performance enhancing substances in athletes and narcotics for drug testing. The test method includes chromatographic-mass spectroscopy.

One such prior art breath collection device includes a thin electrostatic-based air filter, which captures and retains submicron bioaerosol particles that originate from the subject's airway lining fluid. In use, the collection device is connected in fluid communication with a plastic bag to receive some of the exhaled breath passing through the collection device. The bag serves two functions. First, inflation of the bag shows that the subject has properly exhaled into the device. Second, when fully inflated, the bag indicates that the minimum amount of exhaled air has passed through the filter to sufficiently collect biological samples.

Figure 1:
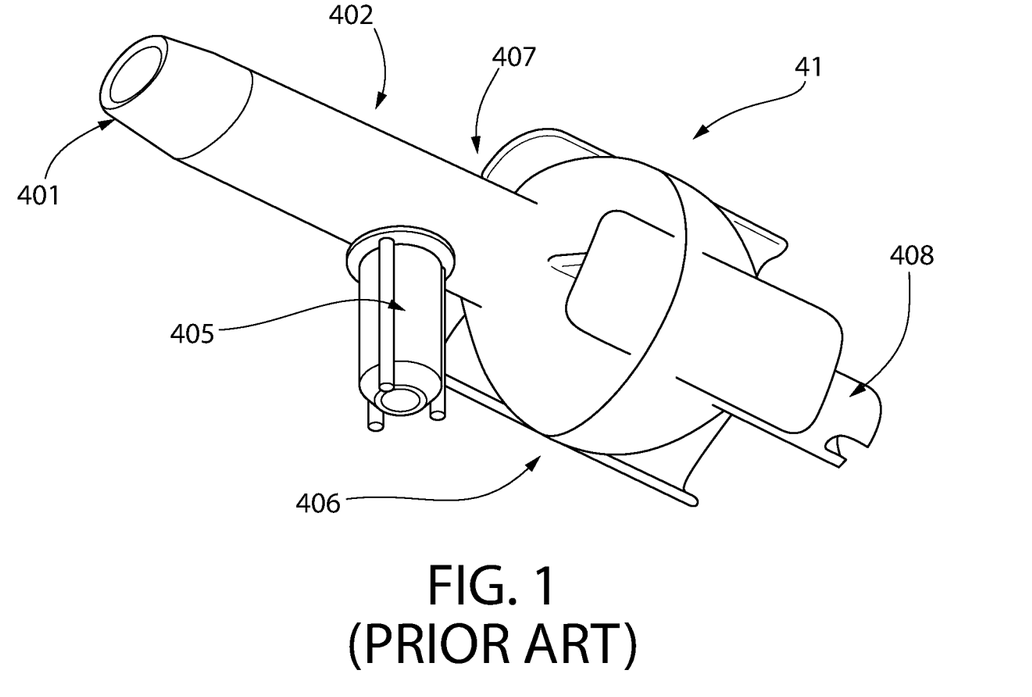
FIG. 1 is perspective view of at least a portion of a prior art system.

To better illustrate an embodiment of the EB system of Sensabues AB, FIG. 1 shows a portable sampling device 41 from FIG. 4B of U.S. Pat. Pub. No. 2014/0366609, which is assembled and ready for use. The device 41 is configured for receiving and containing biological samples from a user's exhaled breath. As shown in FIG. 1, the device 41 includes a mouthpiece section 401 with an inlet, a selective trap section 402 and an extraction port 404 (see FIG. 2B) configured to provide a fluid connection to a plastic bag (discussed below) via an adapter 405. The device 41 further includes an inlet 407 to a housing 406 and an outlet 408 from the housing 406.

Figure 2A:
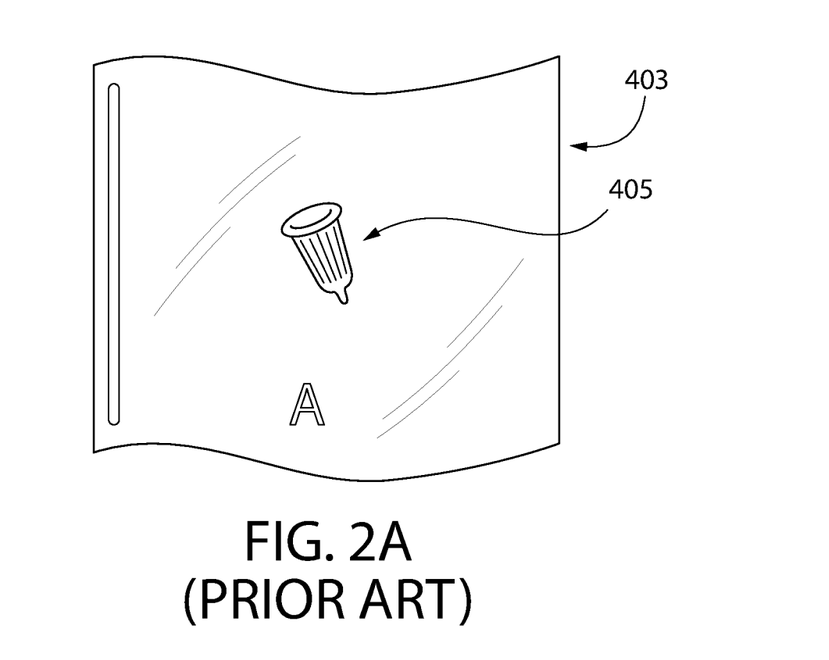
FIGS. 2A-2E are perspective views of various components of the prior art.
Figure 2B:
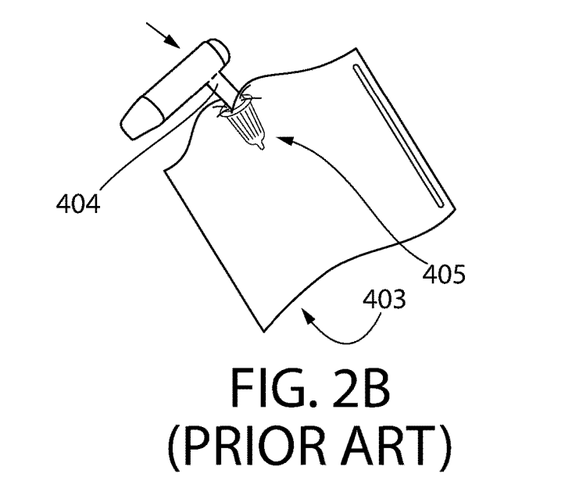
Figure 2C:
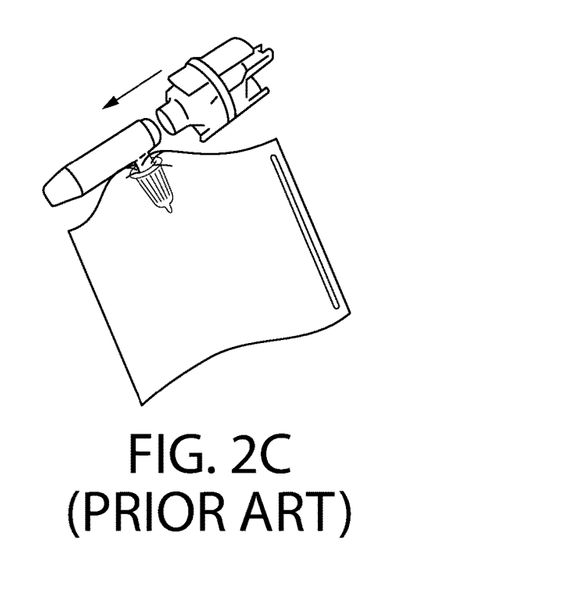
Figure 2D:
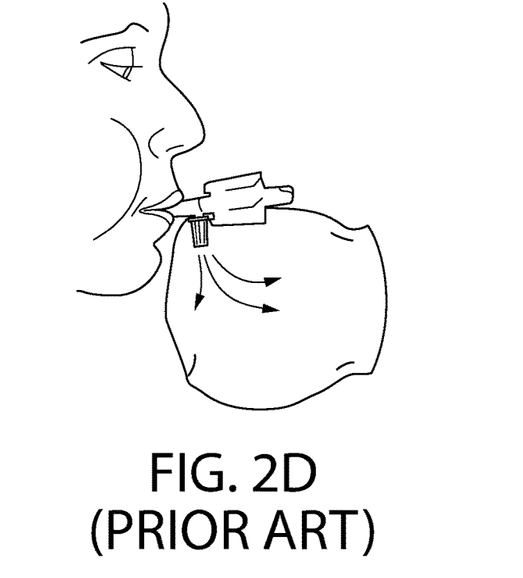
Figure 2E:
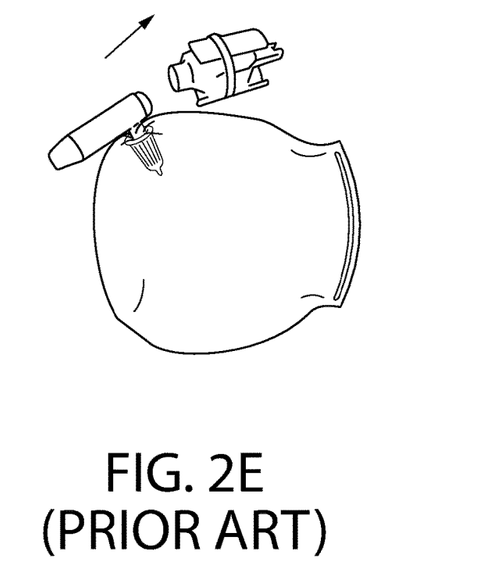

FIGS. 2A-2E show images of the EB system from user instructions provided by Sensabues AB. The EB system includes an inflatable bag with an adapter loosely stored therein (FIG. 2A). The device 41 of FIG. 1 is configured to link-up with the bag of FIG. 2A. FIGS. 2B and 2C illustrate assembly of the device 41 and securing of the same to the bag. In FIG. 2B, the mouthpiece is secured to the bag by puncturing a pointed or sharp end of an extraction port 404 through the bag and directly into an adapter loosely stored therein. Next, as shown in FIG. 2C, the housing 406 is secured to the mouthpiece section 401 and is in fluid communication therewith. FIG. 2D shows a user exhaling into the mouthpiece section 401, which causes biological samples from the exhaled air to be trapped and contained within the housing 406. Diverted exhaled air travels through the port, causing the bag to inflate. Once the pre-determined number of exhaled breaths have been made into the device 41, the housing 406 is separated from the mouthpiece section 401 and is packaged and sent for laboratory analysis.

While the above-described device of the prior art is certainly beneficial and provides a convenient means for biological testing, its construction is not optimal in certain respects. For one, the need to puncture the bag with the port and access the loose adapter within the bag can be troublesome for some users, and may not provide a reliable seal between the port and the bag. Further, the bulbous configuration of the housing 406 may be difficult for a user to reliably grip during use. In addition, the prior art does not include a tamper evident mechanism to indicate whether the housing, after containing a biological sample, was improperly accessed or otherwise tampered with.

BRIEF SUMMARY

Accordingly, the presently disclosed technology overcomes the above and other drawbacks of the prior art, and satisfies the above-outlined and other objectives.

In one aspect, the presently disclosed technology is directed to a system for collecting and retaining a sample from exhaled breath of a subject for analysis. The system includes a housing having a first portion removably attachable to a second portion. The first portion includes an inlet and the second portion includes an outlet.

In another aspect, the presently disclosed technology is directed to a system for collecting and retaining a sample from exhaled breath of a subject for analysis. The system includes a trap section having a first portion and a second portion. The trap section includes a mouthpiece at one end thereof and an outlet at an opposing end thereof. The outlet is configured to removably attach to the inlet of the housing. The trap section further includes an extraction port.

In another aspect, the presently disclosed technology is directed to a system for collecting and retaining a sample from exhaled breath of a subject for analysis. The system includes a fitment having a shaft portion and a winged portion. The shaft portion can be configured to surround at least a portion of the extraction port of the trap section. An exterior surface of the shaft portion includes at least one rib extending perpendicularly to a longitudinal axis of the shaft portion.

In another aspect, the presently disclosed technology is directed to a system for collecting and retaining a sample from exhaled breath of a subject for analysis. The system includes a bag surrounding a winged portion of a boat fitment.

Optionally, the presently disclosed technology is directed to a portable fluid sampling device having a housing including a first portion removably attachable to a second portion. The first and second portions can be configured to combine to form a chamber therein. The chamber can be configured to at least temporarily hold a biological sample therein. At least one of the first portion and the second portion includes an inlet. The other of the first portion and the second portion includes an outlet. Optionally, the device comprises at least one of the following: a) at least one of the first portion and the second portion can include an end having a projection, the other of the at least one of the first portion and the second portion can include an end having a groove configured to receive at least a portion of the projection therein; or b) tamper evident means for indicating that the first portion of the housing has previously been separated from the second portion of the housing.

BRIEF DESCRIPTION OF SEVERAL VIEWS OF THE DRAWINGS

The foregoing summary, as well as the following detailed description of the presently disclosed technology, will be better understood when read in conjunction with the appended drawings, wherein like numerals designate like elements throughout. For the purpose of illustrating the presently disclosed technology, there are shown in the drawings various illustrative embodiments. It should be understood, however, that the presently disclosed technology is not limited to the precise arrangements and instrumentalities shown. In the drawings.

DETAILED DESCRIPTION

While systems, devices and methods are described herein by way of examples and embodiments, those skilled in the art recognize that the systems, devices and methods of the presently disclosed technology are not limited to the embodiments or drawings described. Rather, the presently disclosed technology covers all modifications, equivalents and alternatives falling within the spirit and scope of the appended claims. Any headings used herein are for organizational purposes only and are not meant to limit the scope of the description or the claims. As used herein, the word "unitary" means a component created or formed as a single, integral piece or unit. That is, a component that includes pieces that are created separately and then coupled together as a unit is not a "unitary" component or body. As used herein, the word "may" is used in a permissive sense (i.e., meaning having the potential to) rather than the mandatory sense (i.e., meaning must). Similarly, the words "include," "including," and "includes" mean including, but not limited to. Unless specifically set forth herein, the terms "a," "an" and "the" are not limited to one element but instead should be read as meaning "at least one." The terminology includes the words noted above, derivatives thereof and words of similar import.

Figure 3:
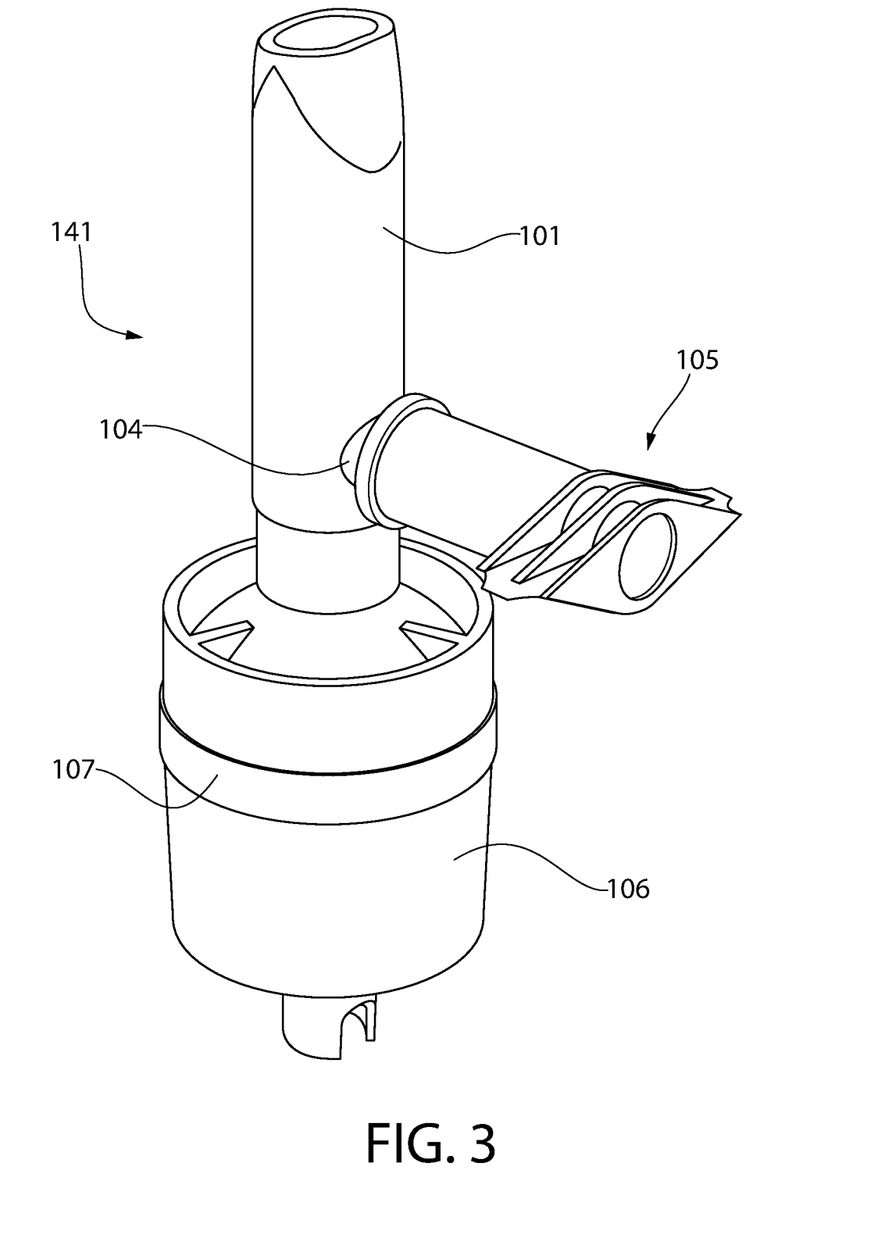
FIG. 3 is an isometric view of an optional embodiment of a device according to an aspect of the disclosed concept.

Referring now in detail to the various figures of the drawings, wherein like reference numerals refer to like parts, there is shown in FIG. 3 an optional embodiment of a device 141 for receiving and containing biological samples from a user's exhaled breath, according to an aspect of the disclosed concept. As with the device 41 in FIG. 1, the device 141 includes a mouthpiece section 101 with an inlet, a selective trap section and an extraction port 104 configured to provide a fluid connection to a plastic bag. The device 141 further includes an inlet to a housing 106 and an outlet from the housing 106.

The device 141 of FIG. 3 includes at least two features that are distinct from features of the device 41 of FIG. 1. First, the housing 106 includes radially extended flange surfaces, which provide an annular and continuous surface 107 around the body of the housing 106. This is an improvement over the bulbous body with discontinuous flanges provided on the device 41 of FIG. 1. The improved design provides a continuous surface 107 that is convenient for ambidextrous use (e.g., for gripping). Further, this renders the housing 106 much easier to grip and hold when a user is exhaling into the device 41. Second, the extraction port 104 of the device 141 is fitted to and/or includes a bag adapter 105 that can comprise a fitment, such as a boat fitment, at a bottom end thereof. The fitment is configured to be sealed within a bag to securely connect the bag adapter 105 to the bag, such that a portion of the adapter 105 extends from within the bag and protrudes through and outside of the bag to facilitate a robust and tight fluid connection between the bag and the adapter 105.

Figure 4:
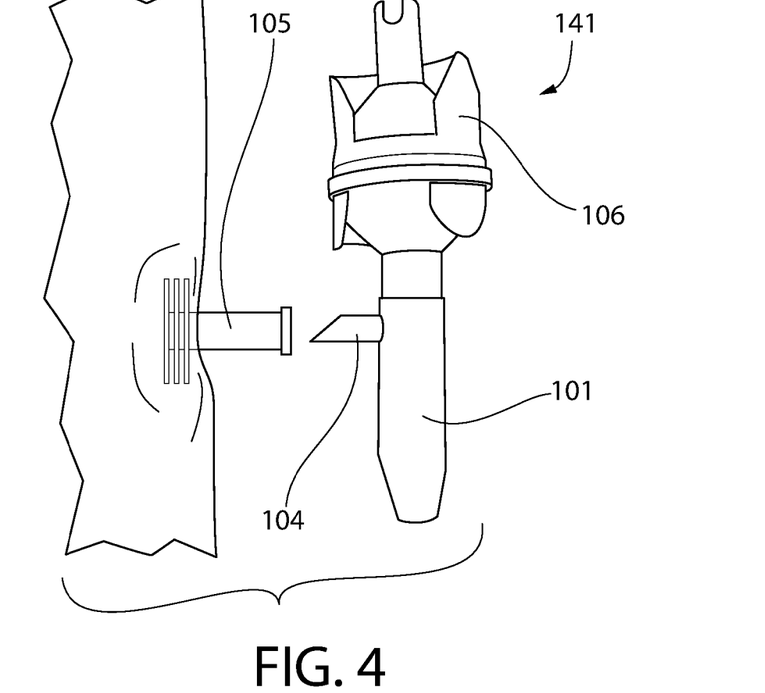
FIG. 4 illustrates a bag having an adapter secured to the bag by a fitment according to one optional embodiment of the presently disclosed technology.

In one embodiment, the fitment may be assembled to an initially open end of a bag. The open end or another portion of the bag may then be sealed around the fitment using thermal energy. This step can be done by a manufacturer. The remainder of the open end of the bag may also be heat sealed, such that the only fluid access to the inside of the bag is through the lumen of the adapter. Optionally, a tight connection between the male extraction port 104 and the adapter may be provided via a slip or taper interference fit. This configuration is easier and more reliable for a user to handle than the conventional design of FIGS. 2A-2E. With FIGS. 2A-2E, a user must puncture the bag and manually guide the loosely held adapter to the point of puncture to connect the port to the adapter and the bag. This can be difficult to do and once achieved, may result in a connection which is not very air tight. By contrast, the concept shown in FIGS. 3 and 4 is much easier for a user to implement and provides a more robust seal between components. That is, the user can more easily connect the parts and there should be relatively minimal, if any, loss of air escaping the bag-device interface during exhalation.

Figure 5A:
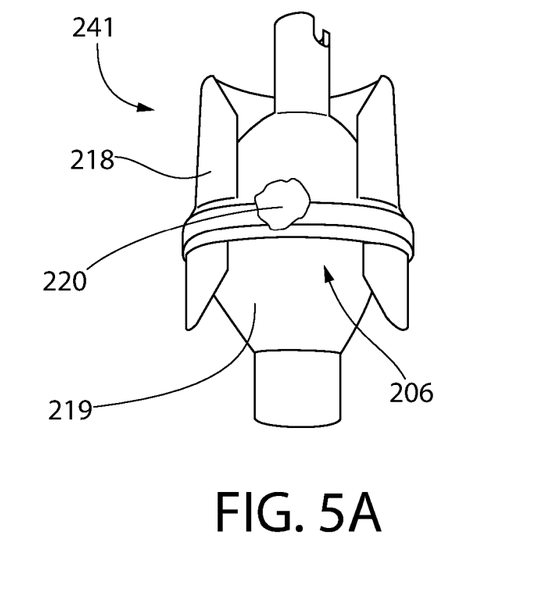
FIGS. 5A and 5B illustrate an optional tamper evident mechanism that may be used in conjunction with a device according to an optional aspect of the disclosed concept.
Figure 5B:
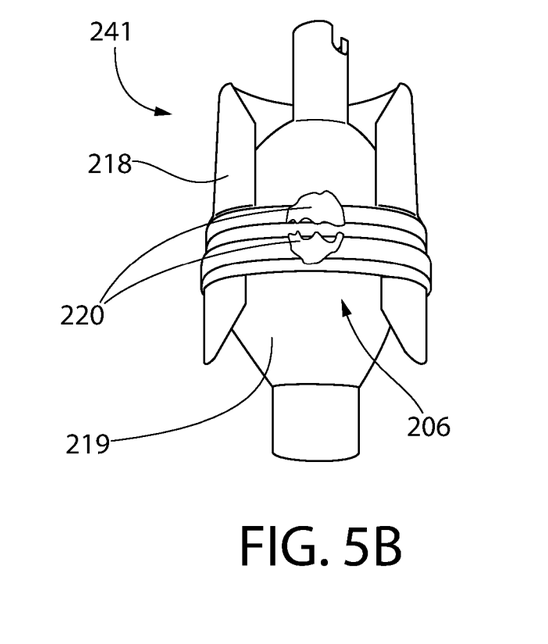

Referring now to FIGS. 5A and 5B, another embodiment of the device 241 can include an optional tamper evident means or feature 220 provided on the housing 206. The housing 206 is configured to trap or at least temporarily hold biological samples from exhaled air within a chamber in the housing. The housing may include an assembly of two components 218, 219 selectively fitted to each other. In one embodiment, the two components 218, 219 are constructed to be resistant to pulling apart. For example, in one optional aspect of the disclosed concept, the two components 218, 219 are snap fit together in such a way as to make it difficult for an individual to manually separate them.

In an optional aspect of the disclosed concept, the tamper evident feature 220 can include a heat stamped symbol or the like that deforms an interface between the two components and/or extends between the two components. In this way, if the components are pulled apart, it is either impossible for one to re-attach them or it is clearly visually evident that the components had previously been pulled apart. This would prevent a person from providing a tampered sample to a laboratory. Alternatively, the tamper evidence means 220 can be in the form of a sticker that extends across to two components 218, 219 of the housing 206. When the housing 206 is opened, the sticker could tear or rip, thereby indicating that the housing 206 had been opened. Regardless of the specific structure used, the tamper evident means 220 indicates that the first portion of the housing 206 has previously been separated from the second portion of the housing 206.

FIGS. 6-10 show another embodiment of the system of the presently disclosed technology. The system can include a device 341 having a housing 306 removably attachable to a trap section 302. The housing 306 includes an inlet 307 (to which the trap section 302 can attach or surround; see FIG. 8) and an outlet 308 (FIG. 6) on an end opposite the trap section 302. The trap section 302 can include a mouthpiece section 301, an extraction port 304, and an outlet section 303. The outlet section 303 can be configured to engage and/or attach to the inlet 307 of the housing 306. An adapter or fitment 305, such as a boat fitment, can be removably attachable to the extraction port 304.

A cap unit 356 can include a first cap 358 attached to a second cap 360 via a plastic, flexible connection strip 361. The first cap 358 can be sized, shaped and/or configured to surround and/or enclose the inlet 307 of the housing 306, and the second cap 360 can be sized, shaped and/or configured to be inserted into or surround and/or enclose the outlet 308 of the housing 306. In any embodiment, such as that shown in FIGS. 6-8, the second cap 360 can include two diametrically opposed projections 362a, 362b. The outlet 308 of the housing 306 can include complementary grooves 364a, 364b (see FIG. 6) that are sized, shaped and/or configured to receive at least a portion of one of the projections 362a, 362b when the second cap 360 closes the outlet 308. In other words, each of the projections 362a, 362b is configured to be located in a corresponding one of the grooves 364a, 364b.

Similar to the benefit of the configuration of the device 141 shown in FIG. 3, the housing 306 has a plurality of annularly spaced-apart ribs 352 that extend around a perimeter, optionally evenly spaced-apart around a perimeter, of the housing 306. In any embodiment, each rib 352 extends parallel to a longitudinal axis of the housing 306 and the trap section 302 when the trap section 302 is properly attached to the housing 306. Each rib 352 can be thickest or widest at or near a mid-section of the housing 306, and can be thinnest or smallest toward proximal and distal ends of the housing 306. Each rib 352 can be divided in half by a collar 354 that extends around an entire periphery of the housing 306 at a mid-section of the housing 306.

Figure 8:
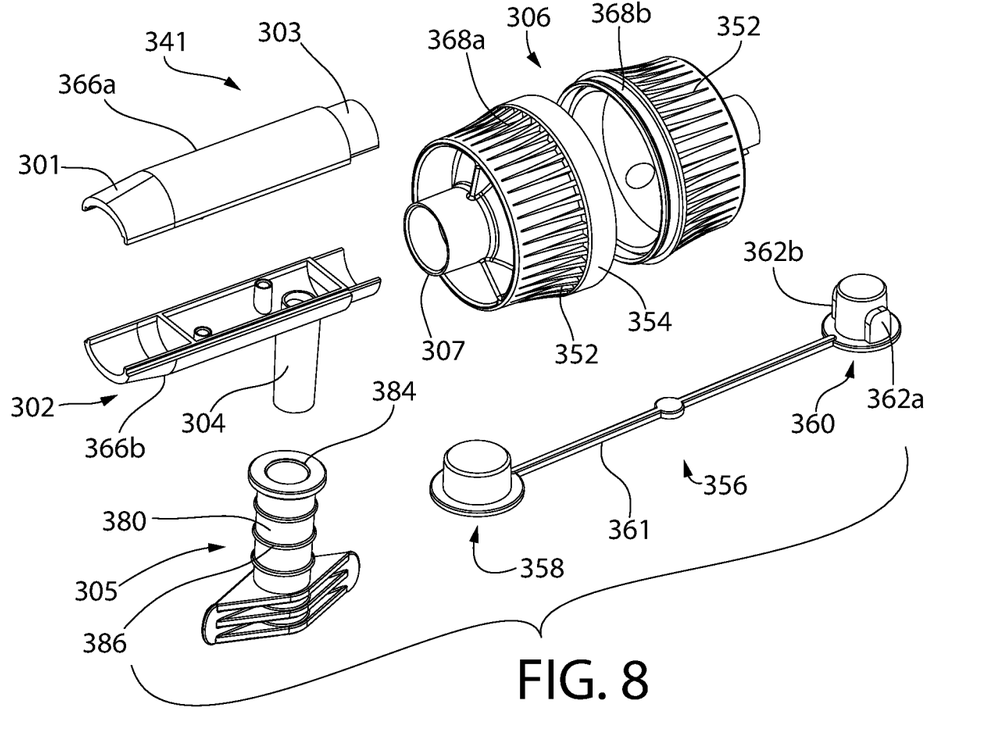
FIG. 8 is a partially exploded isometric view of the system of FIG. 6.

As shown in FIG. 8, the trap section 302 can be formed of two separable components. In any embodiment, the two components can be snap-fitted together. More particularly, the trap section 302 can include a first portion 366a and a second portion 366b. The first portion 366a can form a top half of the trap section 302, and the second portion 366b can form a bottom half of the trap section 302. This two-part design of the trap section 302 is advantageously easier to mold than a design in which two parts are connected by a living hinge. More specifically, the first portion 366a, the second portion 366b, and/or the adapter 305 can advantageously be molded as a unitary component made from one single piece of material. Accordingly, after being molded and set, the first and second portions 366a, 366b and adapter 305 can be separated and assembled together in a relatively simple manner.

Figure 9:
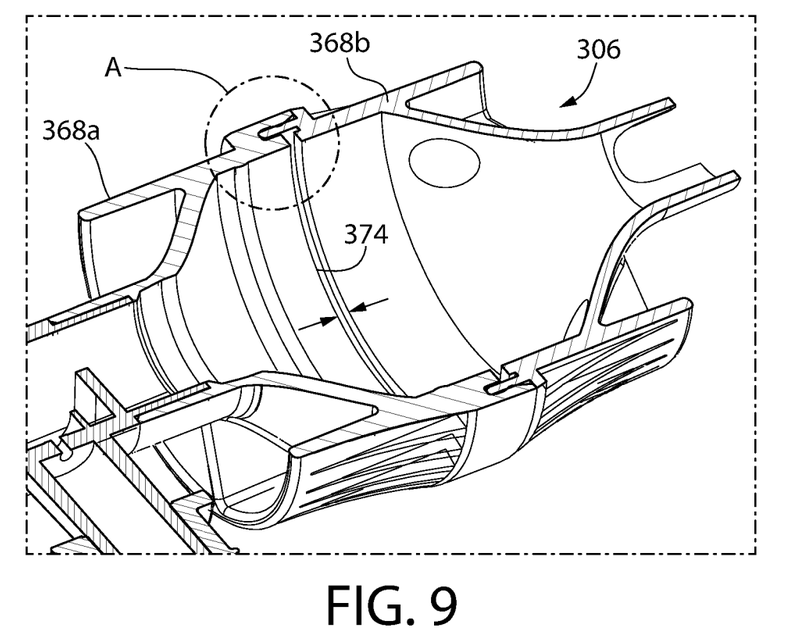
FIG. 9 is a cross-section of a portion of a device of the system of FIG. 6.
Figure 10:
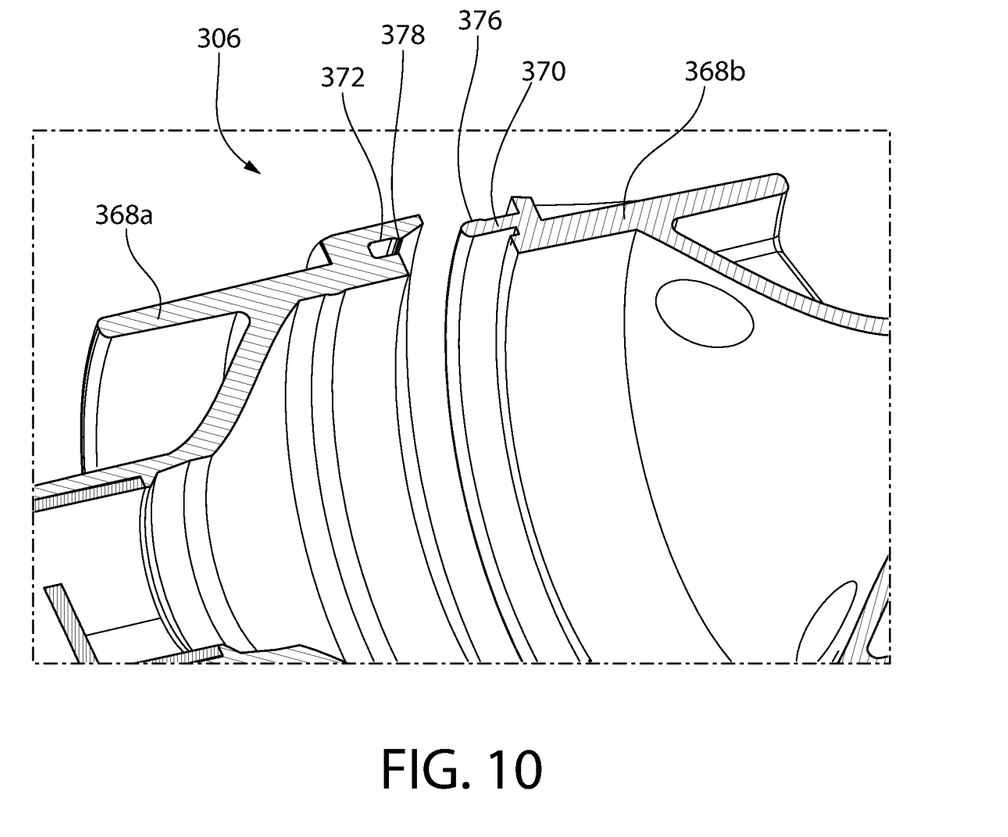
FIG. 10 is a magnified exploded view of a section of section A of FIG. 9.
Figure 11:
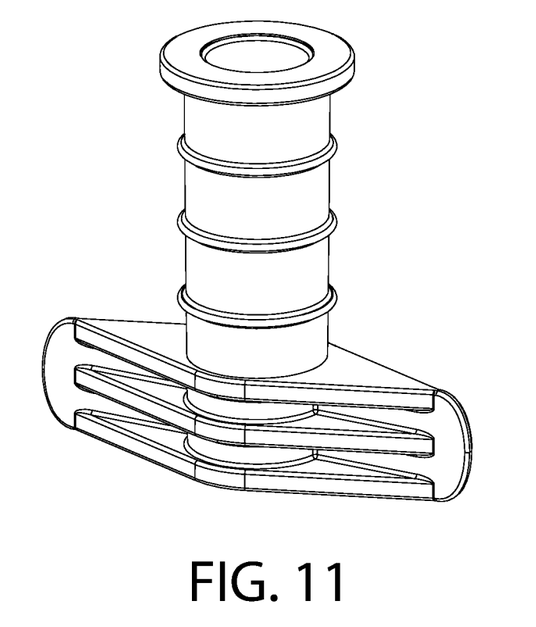
FIGS. 11 and 12 are isometric views of an adapter for the system of FIG. 6.
Figure 12:
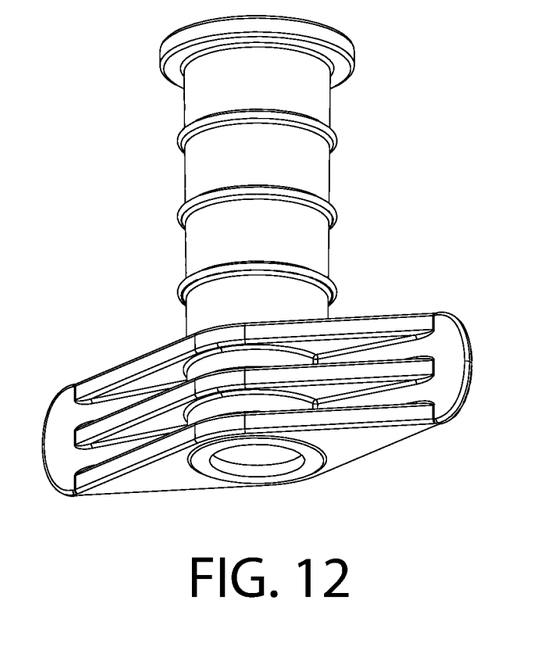
Figure 13:
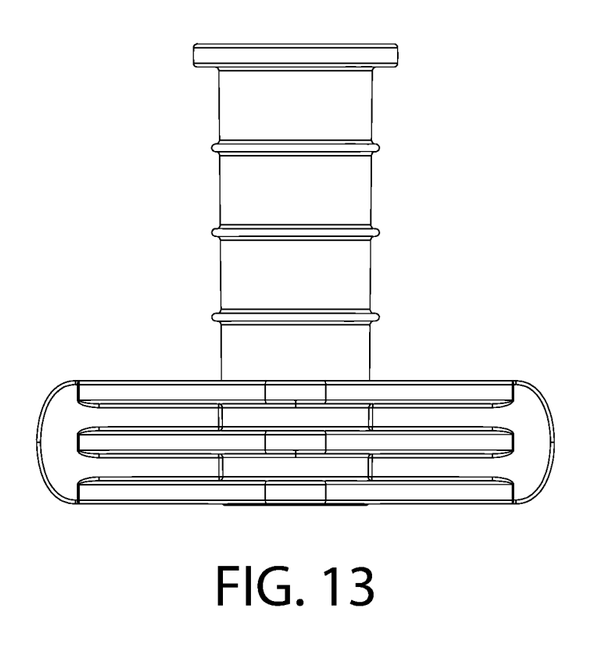
FIG. 13 is a front elevation view of the adapter of FIGS. 11 and 12.
Figure 14:
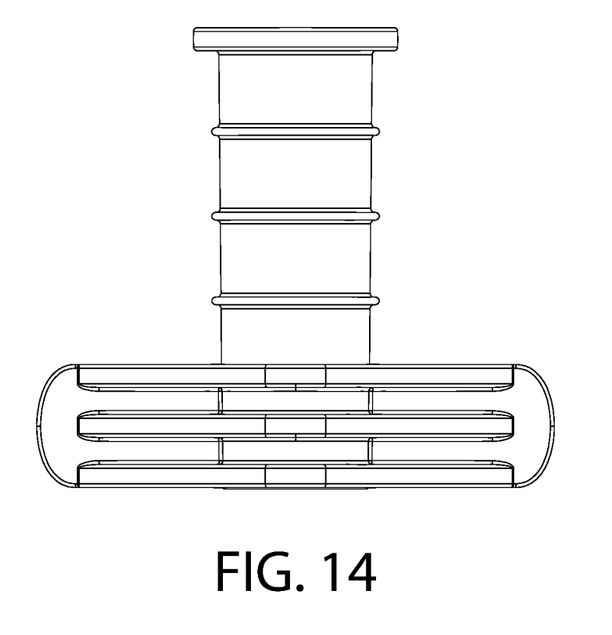
FIG. 14 is a back elevation view of the adapter of FIGS. 11 and 12.
Figure 15:
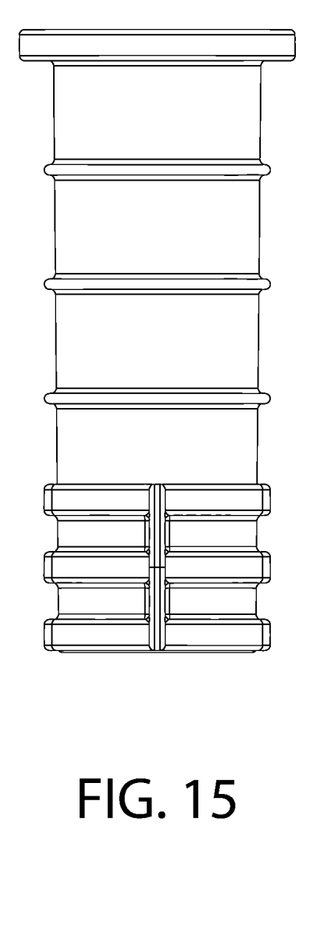
FIG. 15 is a left side elevation view of the adapter of FIGS. 11 and 12.
Figure 16:
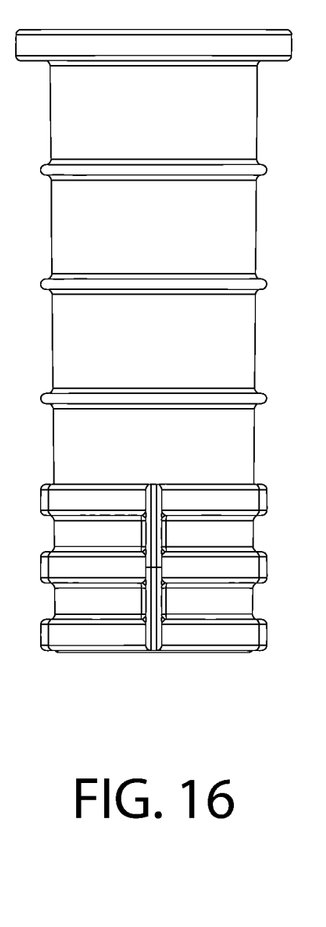
FIG. 16 is a right side elevation view of the adapter of FIGS. 11 and 12.
Figure 17:
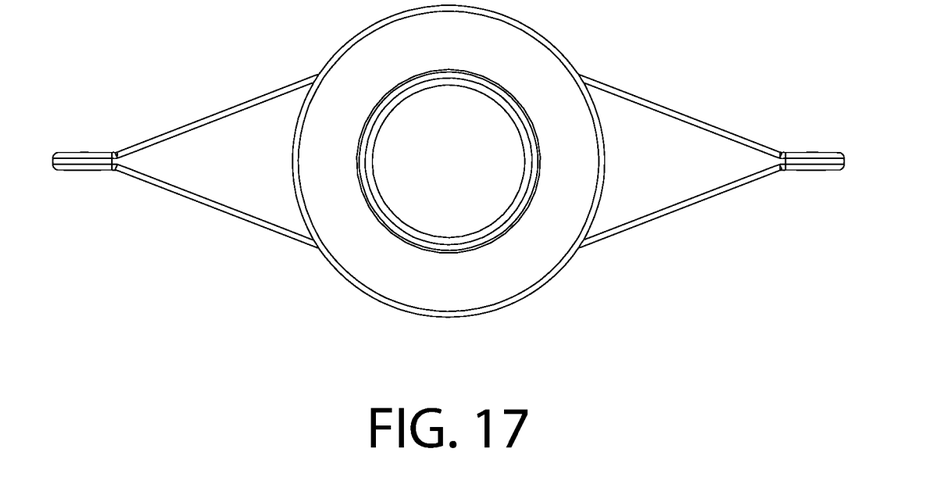
FIG. 17 is a top plan view of the adapter of FIGS. 11 and 12.
Figure 18:
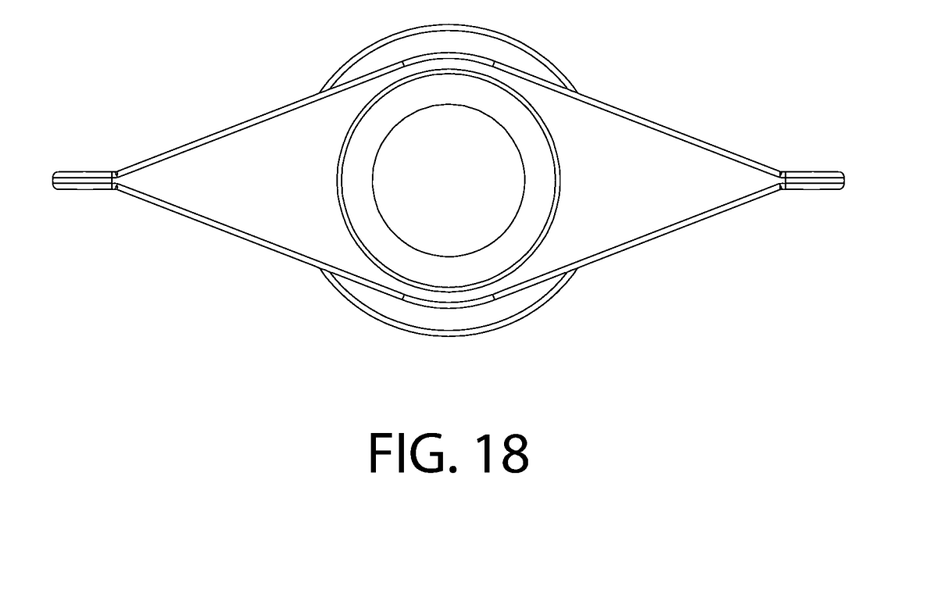
FIG. 18 is a bottom plan view of the adapter of FIGS. 11 and 12.

Referring to FIGS. 8-10, the housing 306 can be formed of two separable components. In any embodiment, the two components can be snap-fitted together. More particularly, the housing 306 can include a first portion 368a removably attachable to a second portion 368b. The first portion 368a can form a front half of the housing 306, and the second portion 368b can form a rear half of the housing 306.

In one embodiment, as shown in FIG. 10, a forward end of the second portion 368b of the housing 306 can include a projection or lip 370. A rear end of the first portion 368a of the housing 306 can include a groove 372. Alternatively, the lip can be on the first portion and the groove can be on the second portion. The groove 372 can be sized, shaped and/or configured to receive at least a portion of the lip 370 therein around an entire periphery of the housing 306. Optionally, the lip 370 can include a bulbous portion 376 at a free end thereof. Optionally, the groove 372 can include a ridge or raised portion 378 therein. In one embodiment, the bulbous portion 376 can contact (e.g., engage) the ridge 378 to prevent (or at least reduce the likelihood of) inadvertent connection or separation of the first and second portions 368a, 368b of the housing 306.

As shown in FIG. 9, when the lip 370 is fully inserted into the groove 372 and/or the first and second portions 368a, 368b of the housing 306 are attached, a gap or spacing 374 can exist between the first and second portions 368a, 368b on an interior of the housing 306. This gap 374 can be sized, shaped and/or configured to receive at least a portion of an outer periphery of a filter or membrane (not shown). The filter can be generally flat or planar, and have a generally circular outer periphery to match an interior shape of the housing 306.

Referring again to FIGS. 6-8, the adapter 305 can have a "T" shape and include a shaft portion 380 and a winged portion 382. The winged portion 382 can include two, spaced-apart wings 382a, 382b, each of which taper away from a mid-section of the winged portion 382. A passageway 384 (see FIG. 8) can extend through the adapter 305 from one end of the shaft portion 380 to an opposing end of the winged portion 382 to allow fluid (e.g., air) to pass therethrough. At least a portion of the extraction portion 304 can sealingly fit within the portion of the passageway 384 defined or surrounded by the shaft portion 380. An exterior surface of the shaft portion 380 can include one or a plurality of spaced-apart annular ribs 386.

In operation, the bag (e.g., made of plastic) surrounds the entire winged portion 382 and at least a portion of the shaft portion 380. Thus, at least a portion of the shaft portion 380 extends outside of the bag. In any embodiment, one or more O-rings (not shown) can surround at least a portion of the bag and the shaft portion 380 of the adapter 305. The O-ring(s) can contact one or more of the ribs 386 to help hold the O-ring in a desired position or location.

As mentioned above, another benefit of the design shown in FIGS. 6-10 is that it is easier to mold the device 341 than other designs in the prior art. For example, the separable components are easier to mold than unitary components.

Figure 6:
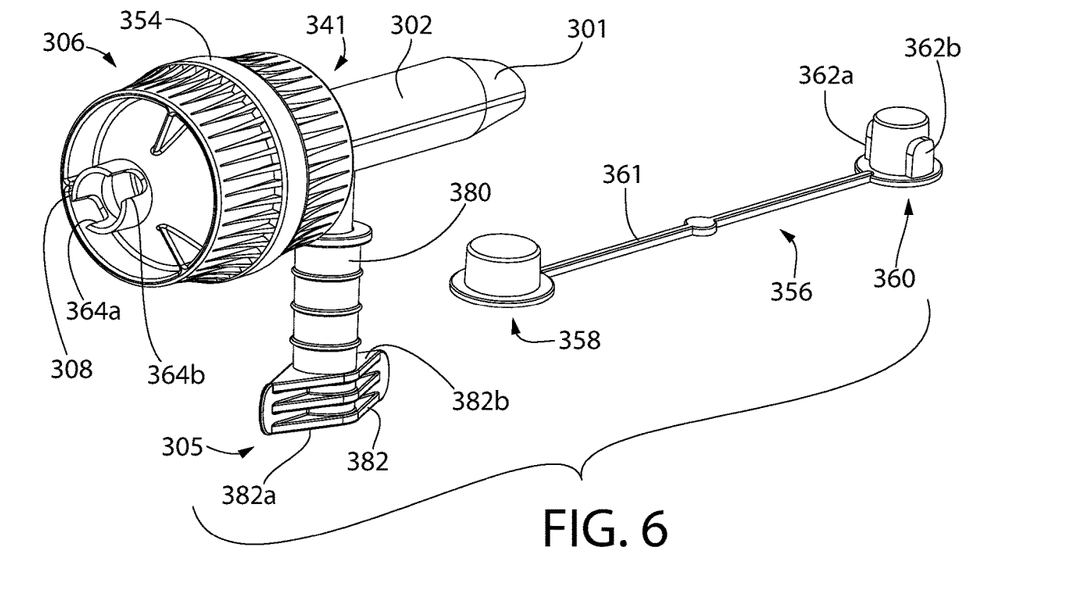
FIG. 6 is an isometric view of an optional embodiment of a system according to an aspect of the disclosed concept.
Figure 7:
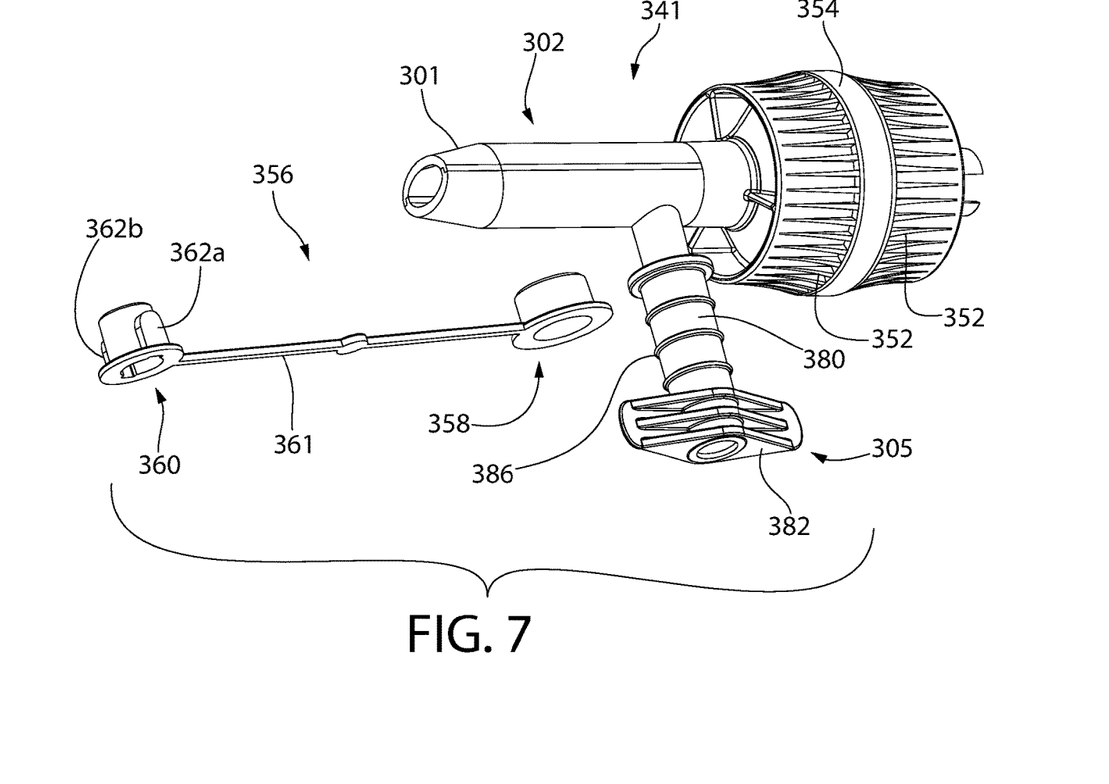
FIG. 7 is another isometric view of the system of FIG. 6.

In operation of one embodiment, the various separable components of the system (see FIG. 8) can be found in a box. An end user, such as an athlete, can open the box and assemble some or all of the components (to form the assembled device, as shown in FIGS. 6 and 7, for example). Once the user has exhaled sufficiently into the device (e.g., indicated by the bag being fully expanded), the user can disassemble the device (except possibly that the two portions of the housing 306 remain attached or connected), and send at least the filter away for laboratory testing.

FIGS. 11-18 show different views of the adapter 305.

Optionally, the presently disclosed technology provides for a portable fluid (e.g., gas) sampling device for collecting aerosols comprising biomarkers from exhaled breath of a subject for further sensor based analysis. By sampling biomarkers from exhaled breath, the device can provide vital information for early detection and/or diagnosis of diseases or illnesses as well as monitoring of disease progression and/or therapy response. Some known non-volatile biomarkers that may be transported by aerosols in exhaled breath includes lipids, peptides, nucleotides, prostanoids, proteins, DNA and/or RNA.

The following exemplary embodiments further describe optional aspects of the presently disclosed technology and are part of this Detailed Description. These exemplary embodiments are set forth in a format substantially akin to claims (each with numerical designations followed by the letter A), although they are not technically claims of the present application. The following exemplary embodiments refer to each other in dependent relationships as "embodiments" instead of "claims."

1A. A portable fluid sampling device, the device comprising:
- a housing including an inlet, an outlet and a chamber therebetween, the housing being configured to trap or at least temporarily hold biological samples from exhaled air within the chamber,
- wherein the housing is configured to be fluidly connected to a bag without requiring the bag to be punctured, e.g., by an end user.

2A. The device of embodiment 1A, further comprising:
- a trap section attachable to the inlet of the housing, the trap section including an extraction port; and
- an adapter removably attachable to at least a portion of the trap section.

3A. The device of embodiment 1A or 2A, wherein the adapter surrounds at least a portion of the trap section.

4A. The device of any one of embodiments 1A-3A, wherein the adapter includes a shaft portion and a winged portion.

5A. The device of any one of embodiments 1A-4A, wherein the winged portion includes two wings, each of which taper away from a mid-section of the winged portion.

6A. The device of any one of embodiments 1A-5A, wherein the adapter is not fixed or otherwise secured to the bag.

7A. The device of any one of embodiments 1A-6A, wherein the adapter does not include a sharp point or spike.

8A. The device of any one of embodiments 1A-7A, wherein the chamber is configured to contain a filter therein.

9A. The device of any one of embodiments 1A-7A, wherein the housing includes a first portion removably attachable to a second portion, and wherein the chamber is configured to fixedly hold a filter therein when the first portion is attached to the second portion.

10A. A portable drug sampling device for handheld collection of a sample from exhaled breath of a subject for further sensor-based analysis, the device comprising:
- two molded components that are removably attachable.

11A. The device according to embodiment 10A, further comprising:
- a permeable sampling membrane positioned inside the housing and arranged transverse to a flow of exhaled breath passing through the housing, the membrane being configured to collect aerosols from the exhaled breath passing through the membrane.

12A. The device according to embodiment 10A or 11A, wherein the membrane comprises at least one layer of non-woven filtration media with a specific weight in the range of 23 $g/m^3$ to 500 $g/m^3$.

13A. A method of screening an individual for the consumption of a particular substance, the method comprising:
- inserting at least a portion of an extraction portion of a trap portion into a portion of a shaft portion of an adapter, a winged portion of the adapter being surrounded by a bag, the trap portion being fluidly connected to a housing containing a member; and
- having an individual blow into the trap portion, thereby directing at least some exhaled breath of the individual into the bag and at least some exhaled breath of the individual through the membrane.

14A. The method according to embodiment 13A, wherein one or more O-rings surround the shaft portion of the adapter.

15A. A method of using a portable fluid sampling device, the method comprising:
- attaching a trap section to a first portion of a housing;
- surrounding a first portion of an adapter with a bag; and
- fluidly connecting a second portion of the adapter to an extraction port of the trap section.

16A. The method of embodiment 15A, further comprising:
- exhaling breath into the trap section.

17A. The method of embodiment 16A, further comprising:
    separating the trap section from the housing after breath is exhaled into the trap section.

18A. The method of any one of embodiment 15A-17A, wherein prior to attaching the trap section to the first portion of the housing, the method comprises:
    attaching the first portion of the housing to the second portion of the housing, the first and second portions combining to surround a membrane.

19A. An adapter configured to fluidly connect a portable fluid sampling device to a volume measure unit, the adapter comprising:
    a tubular element having a first end disposed within the bag and a second end projecting outside of the bag, the first end including a boat fitment, the second end being configured to be secured in fluid communication with an open end of an extraction port of the portable fluid sampling device to facilitate flow of a portion of the exhaled breath into the volume measure unit.

20A. The adapter according to embodiment 19A, wherein the boat fitment includes a shaft portion and a winged portion, the shaft portion surrounding at least a portion of the extraction port of the trap section, an exterior surface of the shaft portion including at least one rib extending perpendicularly to a longitudinal axis of the shaft portion.

21A. The adapter according to embodiment 19A or 20A, wherein the volume measure unit is a plastic bag.

While the presently disclosed technology has been described in detail and with reference to specific examples thereof, it will be apparent to one skilled in the art that various changes and modifications can be made therein without departing from the spirit and scope thereof. It is understood, therefore, that the presently disclosed technology is not limited to the particular embodiments disclosed, but it is intended to cover modifications within the spirit and scope of the present presently disclosed technology as defined by the appended claims.

What is claimed is:

1. A portable fluid sampling device comprising:
    a housing including a first portion removably attachable to a second portion, the first and second portions being configured to combine to form a chamber therein, the chamber being configured to at least temporarily contain or hold a biological sample therein, at least one of the first portion and the second portion including an inlet, the other of the first portion and the second portion including an outlet,
    wherein the device further comprises:
    a) one of the first portion and the second portion including an end having a projection, the other of the first portion and the second portion including an end having a groove, the groove being configured to receive at least a portion of the projection therein; and
    b) a heat stamped symbol on an exterior of each of the first and second portions of the housing, the heat stamped symbol being configured to indicate that the first portion of the housing has previously been separated from the second portion of the housing,
    wherein the projection includes a bulbous portion at a free end thereof, wherein the groove includes a ridge therein, and wherein the bulbous portion is configured to engage the ridge in order to minimize inadvertent separation of the first and second portions of the housing, and
    wherein the housing includes a plurality of annularly spaced-apart ribs that extend around a perimeter of the housing, each rib extending parallel to a longitudinal axis of the housing, each rib being divided in half by a collar that extends around a periphery of the housing at a mid-section of the housing.

2. The device according to claim 1, further comprising:
    a trap section including a mouthpiece at one end thereof and an outlet at an opposing end thereof, the outlet being configured to removably attach to the inlet of the housing, the trap section further including an extraction port.

3. The device according to claim 1, wherein the projection and the groove extend around a periphery of the housing.

4. The device according to claim 1, wherein the first portion of the housing and the second portion of the housing are configured to be snap-fitted together.

5. The device according to claim 2, wherein the trap section comprises a first portion configured to be removably coupled to a second portion.

6. The device according to claim 5, wherein the first portion of the trap section and the second portion of the trap section are configured to be snap-fitted together.

7. The device according to claim 2, wherein fluid is configured to flow into the device through the mouthpiece of the trap section, into the housing through the inlet and out of the trap section through the extraction port.

8. The device according to claim 1, further comprising:
    a permeable sampling membrane positioned inside the housing and arranged transverse to a flow of exhaled breath passing through the housing.

9. A system for collecting and retaining a sample from exhaled breath of a subject for analysis, the system comprising:
    a portable sampling device according to claim 2; and
    a volume measure unit comprising a bag and an adapter, the adapter including a tubular element having a first end disposed within the bag and a second end projecting outside of the bag, the first end including a boat fitment, the second end being configured to be secured in fluid communication with an open end of the extraction port to facilitate flow of a portion of the exhaled breath into the bag.

10. The system according to claim 9, wherein the boat fitment includes a shaft portion and a winged portion, the shaft portion surrounding at least a portion of the extraction port of the trap section, an exterior surface of the shaft portion including at least one rib extending perpendicularly to a longitudinal axis of the shaft portion.

11. The system according to claim 9, wherein the boat fitment is fixed to a portion of the bag.

12. A system for collecting and retaining a sample from exhaled breath of a subject for analysis, the system comprising;
    a portable sampling device comprising:
        a housing including a first portion removably attachable to a second portion, the first and second portions being configured to combine to form a chamber therein, the chamber being configured to at least temporarily contain or hold a biological sample therein, at least one of the first portion and the second portion including an inlet, the other of the first portion and the second portion including an outlet,
        wherein the device further comprises:
        a) one of the first portion and the second portion including an end having a projection, the other of the first portion and the second portion including an end having a groove, the groove being configured to receive at least a portion of the projection therein; and b) a heat stamped symbol on an exterior of each of the first and second portions of the housing, the heat stamped symbol being configured to indicate that the first portion of the housing has previously been separated from the second portion of the housing; and a volume measure unit comprising a bag and an adapter, the adapter including a tubular element having a first end disposed within the bag and a second end projecting outside of the bag, the first end including a boat fitment, the second end being configured to be secured in fluid communication with an open end of an extraction port to facilitate flow of a portion of the exhaled breath into the bag, wherein the boat fitment includes a cylindrical shaft portion and a winged portion at one end of the shaft portion, the cylindrical shaft portion surrounding at least a portion of the extraction port of a trap section, an exterior surface of the cylindrical shaft portion including at least two spaced-apart annular ribs extending perpendicularly to a longitudinal axis of the cylindrical shaft portion, and wherein the winged portion of the boat fitment includes two spaced-apart wings, each wing tapering at a constant slope away from a mid-section of the winged portion.

13. A system for collecting a sample from exhaled breath of a subject for analysis, the system comprising:

a portable sampling device comprising:
  i. a housing comprising at least one inlet and at least one outlet for exhaled breath of a subject to flow through, the housing having an internal chamber configured to receive and retain a sample from the subject's exhaled breath, the housing surrounding a sampling membrane disposed therein, the sampling membrane being configured to collect aerosols from the exhaled breath;
  ii. a first tubular element having a mouthpiece section for the subject to exhale into, the first tubular element being secured to and in fluid communication with the housing; and
  iii. an extraction port arranged downstream of the mouthpiece and upstream of the sampling membrane, the extraction port being configured to divert at least a portion of the exhaled breath into a volume measure unit with which the extraction port is in fluid communication;

the volume measure unit comprising a bag; and an adapter comprising a second tubular element having a first end disposed within the bag and a second end projecting outside of the bag, the first end of the second tubular element comprising a cylindrical shaft portion and a winged portion at one end of the shaft portion, the cylindrical shaft portion surrounding at least a portion of the extraction port, an exterior surface of the cylindrical shaft portion including at least two spaced-apart annular ribs extending perpendicularly to a longitudinal axis of the cylindrical shaft portion, the winged portion including two spaced-apart wings, each wing tapering at a constant slope away from a mid-section of the winged portion, the second end being in fluid communication with an open end of the extraction port of the device to facilitate flow of the at least a portion of the exhaled breath into the bag.

14. The system according to claim 13, wherein the second end of the second tubular element comprises a fitting configured to be secured in fluid communication with the open end of the extraction port to facilitate flow of the at least a portion of the exhaled breath into the bag.

15. The system according to claim 13, wherein the plastic bag is sealed around the first end of the second tubular element via thermal energy.

16. The system according to claim 13, wherein a secure connection is provided between the extraction port and the adapter via slip or taper interference fit.

* * * * *